United States Patent [19]

Fournier

[11] Patent Number: 4,659,067

[45] Date of Patent: Apr. 21, 1987

[54] IMPLANT FOR COXOFEMORAL PROSTHESIS

[76] Inventor: Jacques A. Fournier, 2, Boulevard Edouard Lachaud, 19100 Brive, France

[21] Appl. No.: 774,586

[22] Filed: Sep. 10, 1985

[30] Foreign Application Priority Data

Sep. 10, 1984 [FR] France .................. 84 13871

[51] Int. Cl.$^4$ .............................................. A61F 2/32
[52] U.S. Cl. .................................................... 623/23
[58] Field of Search ................. 623/16, 17, 18, 19, 623/20, 21, 22, 23

[56] References Cited

U.S. PATENT DOCUMENTS 4,199,824 4/1980 Niederer .......................... 623/23

FOREIGN PATENT DOCUMENTS

| 2839661 | 9/1979 | Fed. Rep. of Germany | 623/22 |
| 3003050 | 7/1981 | Fed. Rep. of Germany | |
| 1287526 | 8/1963 | France | |
| 2194123 | 2/1974 | France | |
| 2242065 | 3/1975 | France | |
| 2295730 | 7/1976 | France | |
| 2299012 | 8/1976 | France | |
| 2419717 | 10/1979 | France | |
| 2528307 | 12/1983 | France | |

Primary Examiner—Richard J. Apley
Assistant Examiner—David Isabella
Attorney, Agent, or Firm—Charles W. Fallow; Martin P. Hoffman; Mitchell B. Wasson

[57] ABSTRACT

An implant for coxofemoral prosthesis comprises a slightly conical approximately straight tail that is to be engaged in the medullary cavity of the femur and a body carrying the lug or neck of a ball-and-socket joint, the body being connected to the tail by an upper part or head formed by at least one inclined projection intended to be applied against the surface of the femur cut after its resection at the level of the large trochanter. The implant is characterized in that the projection predominates over the anterior and posterior faces of the tail, and is greatly inclined from the side of the internal cortical wall to constitute a sliding shoe, allowing automatic placing of the implant on the inside the medullary canal.

5 Claims, 6 Drawing Figures

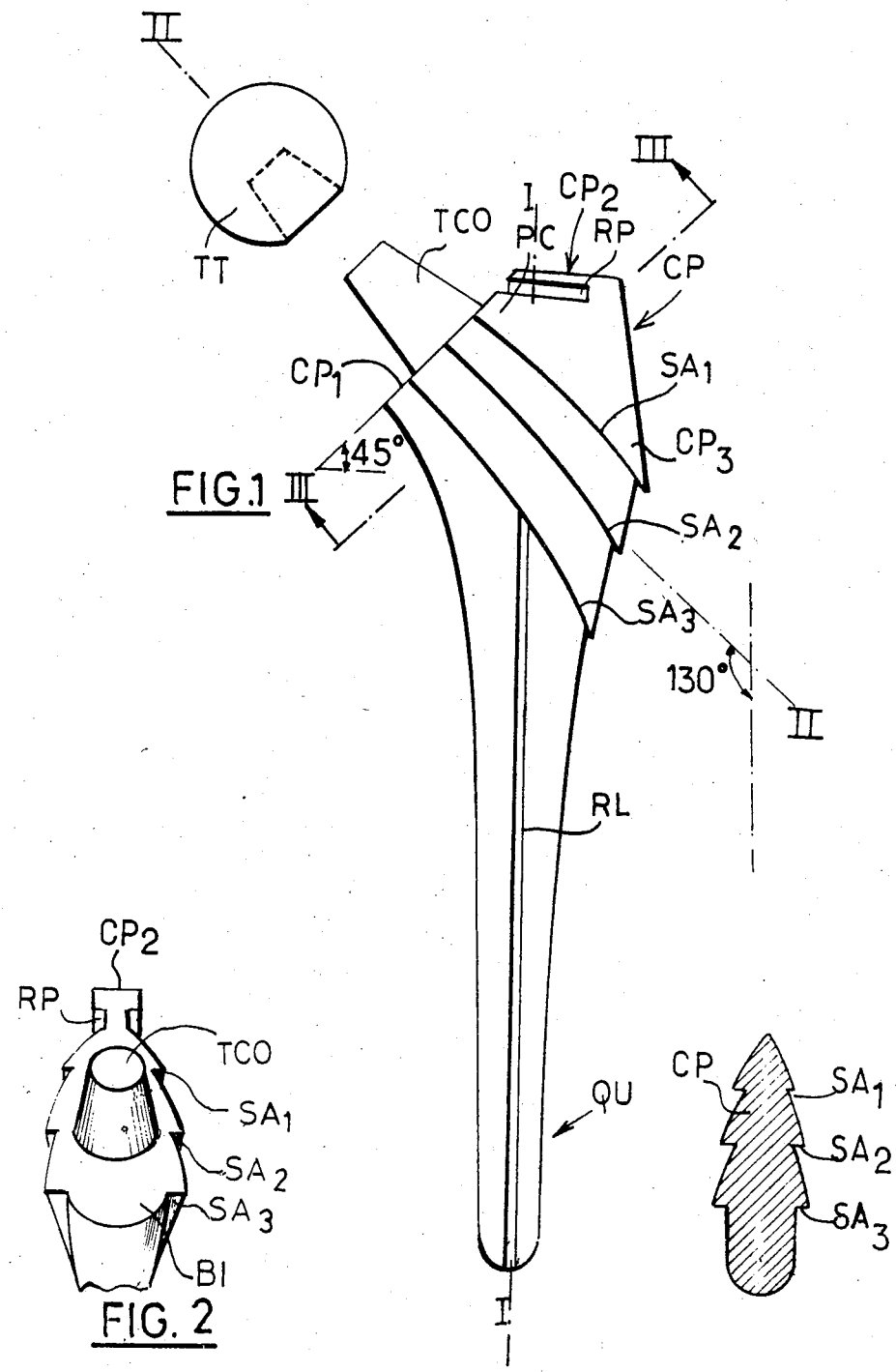

IMPLANT FOR COXOFEMORAL PROSTHESIS

BACKGROUND OF THE INVENTION

The invention relates to a coxofemoral prosthesis comprising an implant intended to be engaged in the medullary cavity of the femur for replacement of both parts of the articulation which has failed for pathological reasons or because of an accident. It is known that a major problem to be solved in such cases is in anchoring of the prosthesis in the femur.

For a little over thirty years, two anchoring techniques have been used, namely: anchoring with a surgical cement, for example, with a methyl methacrylate base; and anchoring without cement, in which case locking is obtained by osteogenesis in contact with the implant in the femoral metaphysis.

It is easy to understand that on the plane of transmission of forces these two techniques are fundamentally different, even though they bring into play structures having certain resemblances between them.

This invention aims at a type of coxofemoral prosthesis of the type not using cement.

These are numerous patents relating to this type of prosthesis. There is found in the prior art the description of implants, often called "pins", more or less curved to follow the axis of the femur in which they are implanted. See, for example, French Pat. Nos. 2,242,065, 2,194,123, 2,528,307, 2,299,012 and 80,495; also West German Pat. No. 3,003,050.

The tail of the implant is either smooth for locking with cement (e.g., No. 2,299,012), or partially smooth (No. 2,528,307) or grained (No. 2,194,123) and generally of circular section, but able to have a cruciform section (No. 80,495) or polygonal section (No. 2,528,307 or No. 2,419,717). Tails are also known provided with a plurality of annular projections like that of an anchor bolt. For example, in No. 2,242,065 or No. 2,295,730, projections are provided perpendicular in relation to the axis of the implant and are intended, in the mind of their inventor, to be perpendicular to the loading force.

Implant prostheses screwed into the medullary cavity can also be cited. It should be noted that in all those cited above, the locking is performed by application of a plate perpendicular to the axis of the implant, on the stump part of the great trochanter or on the cervicotrochanterian fracture as in the case of No. 2,528,307.

Clinical observations have shown that prostheses with a slightly curved tail, plate and projections perpendicular to the axis of the implant were not free from drawbacks and in no way met the expectations of their inventor. We can point out a course failure after short or long term, and a bad distribution of pressure.

The curved profile itself may produce a varus shifting of the tail, driving at higher pressure on the internal cortical (frontal plane) and almost a complete loss in the sagittal plane, and a possibility of fracture of the tail or of internal shifting with cortical reaction at its level.

The poor orientation of the projections can result in microfractures of the osseous neoformations able to cause the implant to migrate, either by sinking in or by releasing it with a painful prosthesis as a consequence.

Further, it should be noted that the presence of crosswise projections make an extraction very difficult in case of a later operation.

The implant according to this invention is conceived according to totally different principles to avoid the above drawbacks. In the present invention, the tail has a straight axis and is slightly conical in shape, and it comprises neither base nor projections perpendicular to this axis but on the contrary, has projections inclined from the internal side to the external side approximately along the axis of the conical lug carrying the ball-and-socket head. These projections, in addition, have a lance shape, i.e., hardly projecting on the internal side, greatly projecting on the anterior and posterior faces, and tapering to a simple tip in the extension of the external cortical wall.

Plainly, the absence of the support plate at the level of the upper part of the prosthesis, on the one hand, and the presence of oblique projections on both the anterior and posterior faces, on the other hand, enable the implant itself to find its place.

Actually, during placing of the prosthesis, these projections guide and orient its sliding, and in the longer term, the spongy bone which is carried and packed against the inside of the cortical wall is transformed into osseous bars which serve as additional support and thus reduce the pressure at the level of the internal cortical wall.

It should also be noted that these osseous bars have the overall direction of force lines of the anterior and posterior cortical walls of the normal femur.

Thus, the artificial support duplicates the natural bone structure in the most anatomical manner possible. In other words, the originality of this prosthesis is, on the one hand, to be an implant whose sliding is controlled by the profile that it exhibits and, on the other hand, to be locked in good position because of its tulip shape both in the frontal plane and in the saggital plane.

It should be noted that this profile fills the available space in the upper part of the femur to be connected, as precisely as possible, along the cortical walls of the upper femoral methaphysis.

Finally, because of its profile, to limit sliding and excessive sinking during placing and impaction of the prosthesis, the internal edge of the latter is more concave than the corresponding femoral cortical wall. Thus, any attempt at excessive impaction will rest on the internal part of the prosthesis which then can only undergo a translation toward the external cortical wall, putting the lance-shaped projections of the external edge of the prosthesis in contact with the external cortical wall of the femur.

All these arrangements contribute, of course, to an extremely powerful blocking especially of possible rotational movements, already greatly limited by the general shape of the upper end of the implant.

Other features and advantages will appear from a reading of the following description taken in conjunction with the accompanying drawings, in which:

BRIEF DESCRIPTION OF THE DRAWINGS

FIG. 1 is an elevation view of a coxofemoral prosthesis comprising the implant according to this invention;

FIG. 2 is a view of the body on the neck side;

FIG. 3 is a section along III—III of FIG. 1;

DESCRIPTION OF THE PREFERRED EMBODIMENT

Referring to FIG. 1, an implant for coxofemoral prosthesis according to the invention comprises a tail QU and a body CP, and a neck formed, on the one hand, by frustoconical lug TCO formed integrally with the body and, on the other hand, by spherical head TT having complementary conical fitting (advantageously a wedging jaw cone whose generatrix forms an angle between 4° and 7° with the axis).

Tail QU has a straight axis I—I in relation to which axis II—II of the neck forms an angle of approximately 130°.

Tail QU comprises longitudinal groove RL cut in at least two lateral faces and intended to allow rising of the bone marrow driven by the conical part as it sinks into the medullary canal. These grooves extend to the lower projection to contain the marrow as much as possible, thus avoiding the creation of excess pressure in this canal and consequently the risks of fat embolism.

The Body CP becomes larger upward in two planes: frontal and sagittal.

The Body CP is limited on the internal side (neck) by a plane surface $CP_1$ perpendicular to axis II—II and on the top by another plane surface $CP_2$ perpendicular to axis I—I.

The Body CP, on internal side BI, extends to tail QU without setback, while it is connected to the tail laterally on the front and back faces by a plurality of projections $SA_1$, $SA_2$, $SA_3$ defining between them steps having sides inclined symmetrically to the median axial plane of the implant.

Figure 4:
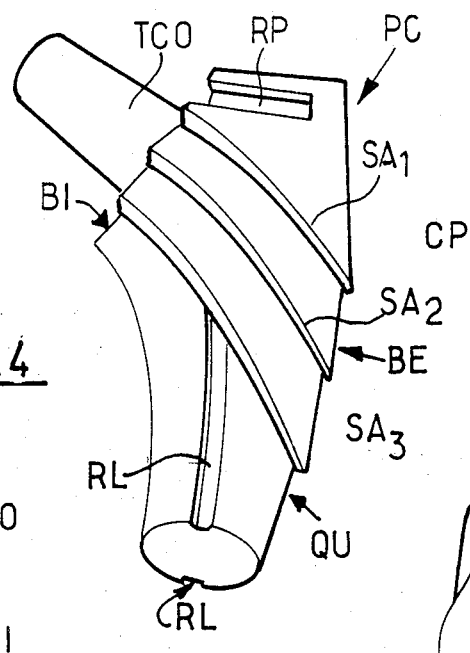
FIG. 4 is a perspective view of the body.
Figure 5:
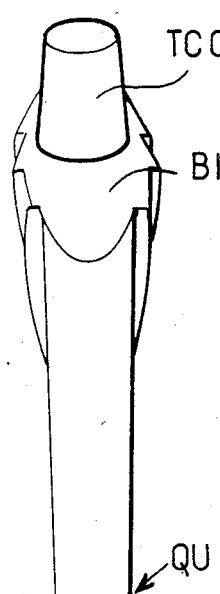
FIGS. 5 and 6 are, respectively, profile views of the implant on the internal side and external side.
Figure 6:
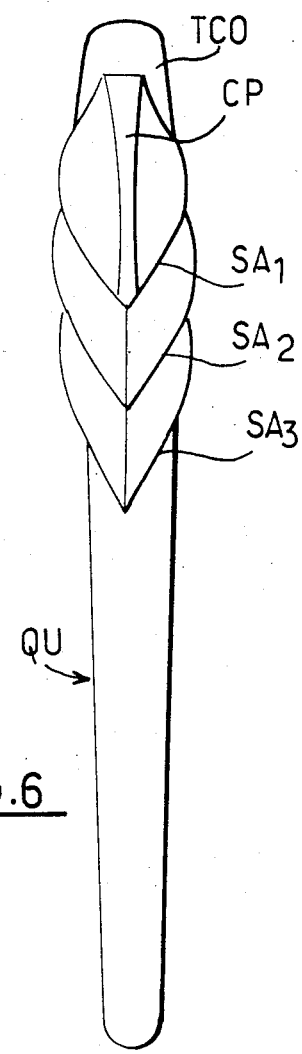

Advantageously, these projections $SA_1$, $SA_2$, $SA_3$, have a lance or almond shape, seen in FIG. 6, as will be described below. The lowest projection $SA_3$, because of its inclination and its shape constitutes a sort of skid or shoe favorable to promoting sliding in the direction of the external cortical wall and thereby putting the implant in place.

External edge BE exhibits an approximately vertical high part $CP_3$ and a low part whose profile curves to meet the external profile of tail QU thus leading to an upward and outward flaring.

Projections $SA_1$, $SA_2$ and $SA_3$ end at this edge and form there, at the level of the external cortical wall of the femur, fastening lugs defined by the junction of the anterior and posterior faces of the projections.

These projections have symmetrical reliefs in relation to the median plane of the implant; they are curved downward starting from surface $CP_1$ to be directed in slightly divergent ways toward external edge BE of the prosthesis where they form the lugs just mentioned.

These projections taper form the high internal edge BI toward the external edge BE. They are made up of two slopes: the upper slope in a gently gradient downward, and the lower slope, abruptly perpendicular to the axis of the implant. As just said, these slopes meet at the level of external edge BE.

In summary, projections $SA_1$, $SA_2$, $SA_3$ have an approximately almond geometric outline, medium on the internal side, wide in the center and almost pointed on the external side.

Two grooves RP are formed on the anterior and posterior faces in the upper part of body CP, allowing grasping of the implant by the impaction tool, which possibly will also be used as an exterior.

Advantageously, the lateral surface of the implant is grained to increase its adherence and its cohesion with the surrounding material.

During introduction of the implant, these reliefs carry the spongy bone, which is packed and gives rise to the formation of osseous bars, on the inside of the femoral metaphysis.

This formation produces three results:

(a) better metaphysical support, distributed over a greater length;

(b) any pressure on the implant causes sliding of this latter toward the external edge, contributing to locking it in an even closer way to the external cortical wall of the femur, and (c) associated with the upward flared shape of the implant, the projections effect a locking mechanism that is greatly improved in comparison with existing implants.

Thus, the prosthesis of this invention by its original design improves the distribution of pressures reduces the usual stresses of hip prostheses (by self-positioning, thanks to its profile and its projections) and locks itself because of its relief stepped like a tulip.

This prosthesis applies in a multipurpose way to femoral articulation surgery (fracture, dysplasia, arthorsis, arthritis).

Inasmuch as the invention is subject to variations and changes in detail, the drawings and the foregoing description should be regarded as only illustrative of the invention defined by the following claims.

What is claimed is:

1. In a coxofemoral implant comprising
a main body portion,
a lug extending from said body portion for mounting an articulating ball thereto, said lug extending along a first axis upward from said body portion and to one side thereof,
a tapered stem extending downward from said body portion along a second axis,
said stem and a said body portion being adapted for placement within the medullary cavity of a femur after resection at the level of the great trochanter, the improvement in combination therewith comprising
at least one anchoring projection on said body portion, said projection being defined by a surface flaring outwardly in the direction of said stem, said surface terminating at a lower edge having an almond shape, and said edge lying in a plane substantially parallel to said first axis and making an angle of approximately 130° with said second axis,
whereby said prosthesis is easily implanted and whereby downward pressure on the implant brings it into contact with the external cortical femoral wall, so as to distribute stresses over a considerable portion of the femur.

2. An implant according to claim 1, wherein below the projection, said stem has on its anterior and posterior faces a longitudinal groove.

3. An implant according to claim 1, wherein said upper part of the body has on its anterior and posterior faces a horizontal groove facilitating grasping of the implant by an impaction tool.

4. An implant according to claim 1, comprising a plurality of said projections, the edges of said projections being substantially parallel.

5. An implant according to claim 4, wherein the projections form a series of steps having sides inclined symmetrically with respect to a plane defined by said first and second axes.

* * * * *